United States Patent
Hirose et al.

(10) Patent No.: US 10,331,809 B2
(45) Date of Patent: Jun. 25, 2019

(54) DEFORMATION ANALYSIS DEVICE, DEFORMATION ANALYSIS METHOD, AND PROGRAM

(71) Applicant: NIPPON STEEL & SUMITOMO METAL CORPORATION, Tokyo (JP)

(72) Inventors: Satoshi Hirose, Tokyo (JP); Toshiyuki Niwa, Tokyo (JP); Yusuke Tsunemi, Tokyo (JP)

(73) Assignee: NIPPON STEEL & SUMITOMO METAL CORPORATION, Tokyo (JP)

(*) Notice: Subject to any disclaimer, the term of this patent is extended or adjusted under 35 U.S.C. 154(b) by 414 days.

(21) Appl. No.: 14/648,951

(22) PCT Filed: Dec. 13, 2013

(86) PCT No.: PCT/JP2013/083483
§ 371 (c)(1),
(2) Date: Jun. 2, 2015

(87) PCT Pub. No.: WO2014/181491
PCT Pub. Date: Nov. 13, 2014

(65) Prior Publication Data
US 2015/0310143 A1   Oct. 29, 2015

(30) Foreign Application Priority Data
May 10, 2013  (JP) ................. 2013-100418

(51) Int. Cl.
*G06F 17/10* (2006.01)
*G06F 17/50* (2006.01)

(52) U.S. Cl.
CPC .......... *G06F 17/5009* (2013.01); *G06F 17/10* (2013.01); *G06F 17/5018* (2013.01);
(Continued)

(58) Field of Classification Search
CPC ... G06F 17/10; G06F 17/5009; G06F 17/5018
(Continued)

(56) References Cited

U.S. PATENT DOCUMENTS

2003/0222871 A1* 12/2003 Brombolich ........ G06F 17/5018
345/427
2008/0141782 A1* 6/2008 Kim ..................... G01N 3/42
73/823
(Continued)

FOREIGN PATENT DOCUMENTS

| JP | 2007-152407 A | 6/2007 |
| JP | 2008-170242 A | 7/2008 |

(Continued)

OTHER PUBLICATIONS

International Preliminary Report on Patentability and Written Opinion of the International Searching Authority (Forms PCT/IB/338, PCT/IB/373 and PCT/ISA/237) for International Application No. PCT/JP2013/083483, dated Nov. 19, 2015.
(Continued)

*Primary Examiner* — Andre Pierre Louis
(74) *Attorney, Agent, or Firm* — Birch, Stewart, Kolasch & Birch, LLP

(57) ABSTRACT

The deformation analysis device includes: a storage unit (12) which stores analysis data of a material; a state variable calculating unit (152) which calculates stresses and other state variables of respective elements of the material at each point in time of deformation of the material, based on the analysis data; a fracture determining unit (153) which, based on the calculated state variables, determines whether or not a fracture has occurred in each of the elements of the material, based on a fracture limit stress curve which is found in advance for the material; and a stress correcting unit (154) which, regarding an element in which it is determined that the fracture has occurred, out of the ele-
(Continued)

ments of the material, reduces σ by the following expression σ=(1−D)σ' where σ is a stress with a rigidity decrease taken into consideration, D is a damage variable (note that 0≤D≤1) in continuum damage mechanics, and σ' is a stress with the rigidity decrease not taken into consideration, to thereby decrease rigidity of the relevant element, without eliminating the element, and updates the analysis data.

3 Claims, 8 Drawing Sheets

(52) U.S. Cl.
CPC .................. *G01N 2203/006* (2013.01); *G01N 2203/0067* (2013.01); *G01N 2203/0218* (2013.01); *G01N 2203/0246* (2013.01); *G06F 2217/16* (2013.01)

(58) Field of Classification Search
USPC ............................................................ 703/2
See application file for complete search history.

(56) References Cited

U.S. PATENT DOCUMENTS

| | | | |
|---|---|---|---|
| 2008/0172211 A1 | 7/2008 | Sakai | |
| 2008/0312882 A1 | 12/2008 | Kumagai | |
| 2009/0119031 A1* | 5/2009 | Niwa | B21D 22/02 702/43 |
| 2009/0177417 A1* | 7/2009 | Yonemura | G01N 3/00 702/42 |
| 2013/0006543 A1* | 1/2013 | Hiwatashi | G01M 5/0033 702/42 |

FOREIGN PATENT DOCUMENTS

| | | | |
|---|---|---|---|
| JP | 2008-310627 A | 12/2008 | |
| JP | 2011-53807 A | 3/2011 | |
| JP | 4980499 B2 | 7/2012 | |

OTHER PUBLICATIONS

Abubakar et al., "Simulation of ship grounding damage using the finite element method," International Journal of Solids and Structures, vol. 50, No. 5, 2013 (available online Nov. 2, 2012), pp. 623-636, XP055293313.
Extended European Search Report, dated Aug. 12, 2014, for counterpart European Application No. 13884149.9.
Hogström et al., "An experimental and numerical study of the effects of length scale and strain state on the necking and fracture behaviours in sheet metals," International Journal of Impact Engineering, vol. 36, No. 10-11, Oct. 2009 (available online May 23, 2009), pp. 1194-1203, XP026319532.
Hogström et al., "An extensive study of a ship's survivability after collision—A parameter study of material characteristics, non-linear FEA and damage stability analyses," Marine Structures, vol. 27, No. 1, 2012, pp. 1-28, XP028481772.
LSTC, "LS-Dyna Keyword User's Manual," vol. II, Material Models, Version 971 R6.1.0, Aug. 2012, pp. 1-18-1-31 (15 pages), XP055293517.
International Search Report, issued in PCT/JP2013/083483, dated Mar. 11, 2014.
Liu et al., "Investigation on Fatigue-Creep Interaction Damage Model for Solder", Proceedings, 2008 International Conference on Electronic Packaging Technology & High Density Packaging (ICEPT-HDP 2008), Jul. 28, 2008, 3 pages.
Liu et al., "Mesh Dependence and Stress Singularity in Local Approach to Creep-Crack Growth Analysis", Transactions of the JSME (Series A), vol. 59, No. 564, Aug. 25, 1993, pp. 1811-1818.
Office Action of Japanese Patent Application No. 2014-526316 dated Jul. 15, 2014.
Wang et al., "Study on Multi-field Coupled Model and Numerical Simulation During Excavation of Tunnel", 2008 International Workshop on Modelling, Simulation and Optimization, Dec. 27, 2008, pp. 334-337.
Written Opinion of the International Searching Authority, issued in PCT/JP2013/083483, dated Mar. 11, 2014.

\* cited by examiner

F I G. 2
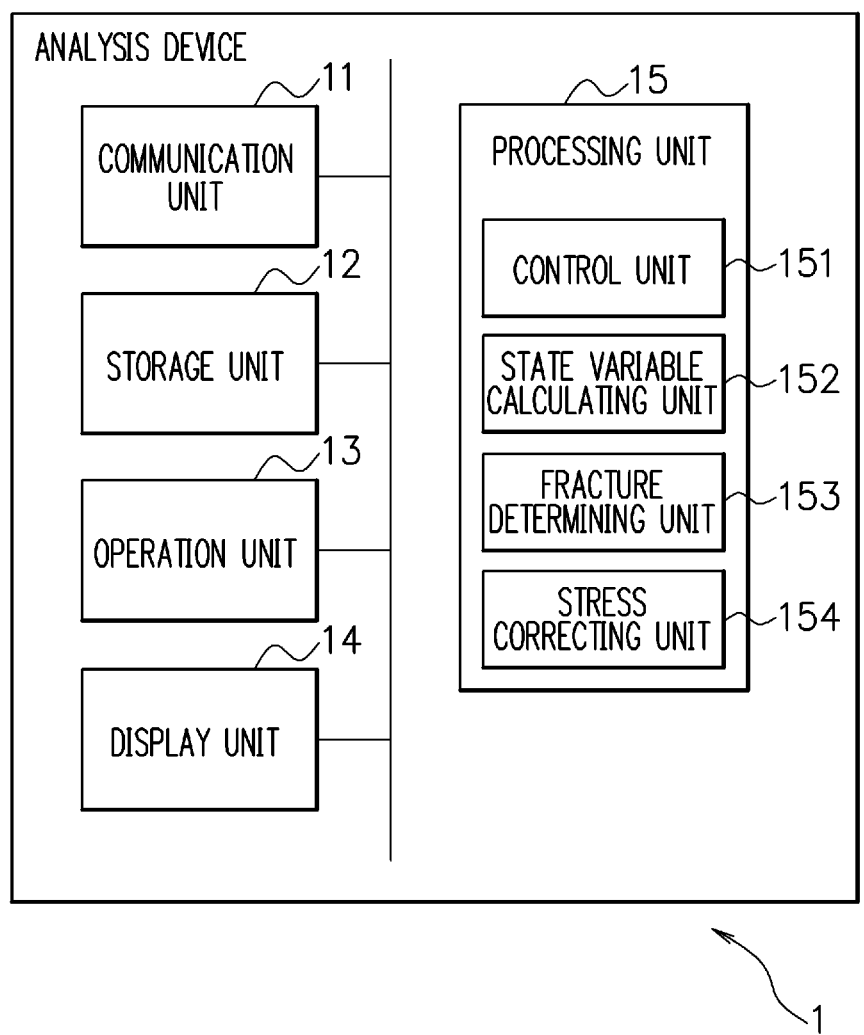

FIG. 3A

| ELEMENT NUMBER | NODAL POINT NUMBER 1 | NODAL POINT NUMBER 2 | NODAL POINT NUMBER 3 | NODAL POINT NUMBER 4 |
|---|---|---|---|---|
| $e_1$ | $n_1$ | $n_2$ | $n_3$ | $n_4$ |
| $e_2$ | $n_5$ | $n_6$ | $n_7$ | $n_8$ |
| ... | ... | ... | ... | ... |

FIG. 3B

| NODAL POINT NUMBER | X COORDINATE | Y COORDINATE | Z COORDINATE |
|---|---|---|---|
| $n_1$ | $xc_1$ | $yc_1$ | $zc_1$ |
| $n_2$ | $xc_2$ | $yc_2$ | $zc_2$ |
| ... | ... | ... | ... |

FIG. 3C

| NODAL POINT NUMBER | X DISPLACEMENT | Y DISPLACEMENT | Z DISPLACEMENT |
|---|---|---|---|
| $n_1$ | $xd_1$ | $yd_1$ | $zd_1$ |
| $n_2$ | $xd_2$ | $yd_2$ | $zd_2$ |
| ... | ... | ... | ... |

FIG. 3D

| NODAL POINT NUMBER | X LOAD | Y LOAD | Z LOAD |
|---|---|---|---|
| $n_1$ | $xl_1$ | $yl_1$ | $zl_1$ |
| $n_2$ | $xl_2$ | $yl_2$ | $zl_2$ |
| ... | ... | ... | ... |

FIG. 5A

| ELEMENT NUMBER | EVALUATION POINT NUMBER 1 | EVALUATION POINT NUMBER 2 | ... | EVALUATION POINT NUMBER 8 |
|---|---|---|---|---|
| $e_1$ | $p_1$ | $p_2$ | ... | $p_8$ |
| $e_2$ | $p_9$ | $p_{10}$ | ... | $p_{16}$ |
| ... | ... | ... | ... | ... |

FIG. 5B

| TIME | NODAL POINT NUMBER | X COORDINATE | Y COORDINATE | Z COORDINATE |
|---|---|---|---|---|
| $t_1$ | $n_1$ | $xc_1$ | $yc_1$ | $zc_1$ |
|  | $n_2$ | $xc_2$ | $yc_2$ | $zc_2$ |
|  | ... | ... | ... | ... |
| ... |  |  |  |  |

FIG. 5C

| TIME | EVALUATION POINT NUMBER | STRAIN | STRESS | FRACTURE FLAG | DAMAGE DEGREE | CUMULATIVE DAMAGE SPEED |
|---|---|---|---|---|---|---|
| $t_1$ | $p_1$ | $sn_1$ | $ss_1$ | $f_1$ | $d_1$ | $ds_1$ |
|  | $p_2$ | $sn_2$ | $ss_2$ | $f_2$ | $d_2$ | $ds_2$ |
|  | ... | ... | ... | ... | ... | ... |
| ... |  |  |  |  |  |  |

| PATTERN | $P_1$ | $P_2$ | $P_3$ | $P_4$ | $P_5$ |
|---|---|---|---|---|---|
| FRACTURE DETERMINATION | × | ○ | ○ | ○ | ○ |
| RIGIDITY DECREASE | × | × | ○ | ○ | ○ |
| DENSITY [kg/mm³] | $7.89 \times 10^{-6}$ | $7.89 \times 10^{-6}$ | $7.89 \times 10^{-6}$ | $7.89 \times 10^{-6}$ | $7.89 \times 10^{-6}$ |
| E[MPa] | 206000 | 206000 | 206000 | 206000 | 206000 |
| $\nu$[−] | 0.333 | 0.333 | 0.333 | 0.333 | 0.333 |
| K[MPa] | 922 | 922 | 922 | 922 | 922 |
| $\varepsilon_0$[−] | 0.006 | 0.006 | 0.006 | 0.006 | 0.006 |
| n[−] | 0.130 | 0.130 | 0.130 | 0.130 | 0.130 |
| S[MPa] | − | − | 14.8 | 7.4 | 4.9 |
| Dc[−] | − | − | 0.20 | 0.20 | 0.20 |

DEFORMATION ANALYSIS DEVICE, DEFORMATION ANALYSIS METHOD, AND PROGRAM

TECHNICAL FIELD

The present invention relates to a deformation analysis device, a deformation analysis method, and a program.

BACKGROUND ART

In the deformation of a material, for example, in press forming of a plate material, it has been known that a forming crack occurs in a formed product if a forming condition is not appropriate. Therefore, there has been used a method in which, by using a computer, the press forming of the plate material is simulated under various forming conditions and validity of the forming conditions is determined based on the result (for example, Patent Literature 1).

In general, such a method repeatedly executes the following three steps until an appropriate forming condition under which no forming crack occurs and also other requirements (for example, weight reduction, thinning, and so on of a product) are satisfied is obtained:

(1) The press forming is simulated under a set forming condition and strains of portions of a material are successively calculated by using the simulation result;

(2) Determination is made regarding the occurrence of a forming crack based on whether or not the calculated strain exceeds FLC (Forming Limit Curve) depicted in FLD (Forming Limit Diagram) prepared in advance for each material; and (3) When it is determined that the forming crack occurs, a forming condition of a portion thought to be a cause of the occurrence of the forming crack is corrected.

Such a method of searching for the appropriate forming condition by the simulation of the press forming with reference to the forming limit diagram is very useful for reducing the cost at a product design stage and shortening a design period.

However, the conventional method determines whether or not the forming crack occurs, simply by referring to the forming limit diagram (proportional deformation FLD) in a case of what is called proportional deformation whose strain direction is always constant, and even if applied to actual press forming accompanied by complicated deformation, the method is not often able to find the appropriate forming condition. In other words, the conventional method is greatly deformation path-dependent and is not applicable to a phenomenon such as a collision causing complicated deformation.

Therefore, in recent years, a method of determining whether or not a forming crack occurs by using a stress (stress FLD) instead of the strain has been developed. For example, Patent Literature 2 discloses a method of estimating a fracture limit curve of a strain space in a proportional load path, converting the fracture limit curve of the strain space to a fracture limit curve of a stress space (fracture limit stress curve), calculating fracture risk by using the fracture limit stress curve, and performing fracture determination based on the calculated fracture risk. Such a method is capable of performing the fracture determination regarding a fracture determination target portion in a process including one deformation path change or more. In other words, such a method is less dependent on the deformation path and is also applicable to a phenomenon such as a collision causing complicated deformation.

Incidentally, in the conventional method, when a fracture occurs in a certain element, a fracture state is expressed by eliminating this element. When some element is eliminated, a stress having been applied to the element is dispersedly applied to elements therearound. Therefore, if the size of the eliminated element is small, the stress applied to its surroundings is also small and a crack gradually progresses, but when the size of the eliminated element is large, the stress applied to elements therearound is large and a crack in the simulation is likely to progress more than actually. Therefore, in the conventional method, it is sometimes difficult to predict a behavior after the occurrence of the fracture.

For example, Patent Literature 3 discloses a method in which, in a collision analysis device which models, by a finite element method, a shock absorber composed of a set of cylindrical bodies whose axes are set parallel to one another, causes the shock absorber to collide with a collision target modeled by a finite element method in a predetermined manner, and analyzes the collision, a correction characteristic is set so as to suppress an increase of a stress in a region where the total drag characteristic expressed by a relation between a stress and a strain at the time of the compression of the modeled shock absorber exceeds a preset strain value. More concretely, it discloses a correction characteristic in which a stress σ decreases in accordance with an increase of a strain ε in a region where the strain ε exceeds ε1. Such a method is capable of naturally and accurately reproducing and analyzing a collision in a wide characteristic range of stress-strain control.

However, Patent Literature 3 does not disclose a concrete way of setting the correction characteristic.

CITATION LIST

Patent Literature

Patent Literature 1: Japanese Laid-open Patent Publication No. 2007-152407

Patent Literature 2: Japanese Patent No. 4980499

Patent Literature 3: Japanese Laid-open Patent Publication No. 2011-53807

SUMMARY OF INVENTION

Technical Problem

As described above, in the conventional methods, it is sometimes difficult to predict a behavior after a fracture occurs.

The present invention was made to solve such a problem, and has an object to enable to make a behavior after the occurrence of a fracture approximate to an actual behavior.

Solution to Problem

A deformation analysis device of the present invention is a deformation analysis device which calculates a state variable indicating a state which occurs in a material according to deformation, the device including:

a storage unit which stores analysis data of the material;

a state variable calculating unit which calculates stresses and other state variables of respective elements of the material at each point in time of the deformation of the material, based on the analysis data;

a fracture determining unit which, based on the calculated state variables, determines whether or not a fracture has occurred in each of the elements of the material, based on a fracture limit stress curve which is found in advance for the material;

a rigidity decreasing unit which, regarding an element in which it is determined that the fracture has occurred, out of the elements of the material, reduces $\sigma$ by the following expression where $\sigma$ is a stress with a rigidity decrease taken into consideration, D is a damage variable (note that $0 \leq D \leq 1$) in continuum damage mechanics, and $\sigma'$ is a stress with the rigidity decrease not taken into consideration, $$\sigma=(1-D)\sigma'$$

to thereby decrease rigidity of the relevant element, without eliminating the element, and updates the analysis data; and an output unit which outputs the calculated state variables.

Another characteristic of the deformation analysis device of the present invention is that, when the damage variable D exceeds a threshold value which is separately decided, the rigidity decreasing unit eliminates the element in which it is determined that the fracture has occurred.

A deformation analysis method of the present invention is a deformation analysis method in which an analysis device including a storage unit which stores analysis data of a material calculates a state variable indicating a state occurring in the material according to deformation, wherein the analysis device:

calculates stresses and other state variables of respective elements of the material at one point in time of the deformation of the material, based on the analysis data;

based on the calculated state variables, determines whether or not a fracture has occurred in each of the elements of the material, based on a fracture limit stress curve which is found in advance for the material;

regarding an element in which it is determined that the fracture has occurred, out of the elements of the material, reduces $\sigma$ by the following expression where $\sigma$ is a stress with a rigidity decrease taken into consideration, D is a damage variable (note that $0 \leq D \leq 1$) in continuum damage mechanics, and $\sigma'$ is a stress with the rigidity decrease not taken into consideration, $$\sigma=(1-D)\sigma'$$

to thereby decrease rigidity of the relevant element, without eliminating the element, and updates the analysis data;

calculates state variables of the respective elements of the material at a subsequent point in time of the deformation of the material, based on the updated analysis data; and outputs the calculated state variables.

Further, another characteristic of the deformation analysis method of the present invention is that, when the damage variable D exceeds a threshold value which is separately decided, the element in which it is determined that the fracture has occurred is eliminated.

A program of the present invention is a program causing a computer including a storage unit which stores analysis data of a material to execute a deformation analysis of calculating a state variable indicating a state occurring in the material according to deformation, the computer being caused to execute:

calculating stresses and other state variables of respective elements of the material at one point in time of the deformation of the material, based on the analysis data;

based on the calculated state variables, determining whether or not a fracture has occurred in each of the elements of the material, based on a fracture limit stress curve which is found in advance for the material;

regarding an element in which it is determined that the fracture has occurred, out of the elements of the material, reducing $\sigma$ by the following expression where $\sigma$ is a stress with a rigidity decrease taken into consideration, D is a damage variable (note that $0 \leq D \leq 1$) in continuum damage mechanics, and $\sigma'$ is a stress with the rigidity decrease not taken into consideration, $$\sigma=(1-D)\sigma'$$

to thereby decrease rigidity of the relevant element, without eliminating the element, and updating the analysis data;

calculating state variables of the respective elements of the material at a subsequent point in time of the deformation of the material, based on the updated analysis data; and outputting the calculated state variables.

Further, another characteristic of the program of the present invention is that, when the damage variable D exceeds a threshold value which is separately decided, the element in which it is determined that the fracture has occurred is eliminated.

Advantageous Effects of Invention

According to the present invention, regarding the element in which it is determined that the fracture has occurred based on a fracture limit stress curve, $\sigma$ is reduced by the following expression where $\sigma$ is a stress with a rigidity decrease taken into consideration, D is a damage variable (note that $0 \leq D \leq 1$) in continuum damage mechanics, and $\sigma'$ is a stress with the rigidity decrease not taken into consideration, $$\sigma=(1-D)\sigma'$$

to thereby decrease rigidity of the relevant element, without eliminating the element, which makes it possible to make a behavior after the fracture occurs approximate to an actual behavior.

BRIEF DESCRIPTION OF DRAWINGS

FIG. 2 is a diagram illustrating an example of a schematic structure of an analysis device.

FIG. 3A is a chart illustrating an example of a data structure of element structure data.

FIG. 3B is a chart illustrating an example of a data structure of nodal coordinate data.

FIG. 3C is a chart illustrating an example of a data structure of displacement condition data.

FIG. 3D is a chart illustrating an example of a data structure of load condition data.

FIG. 5A is a chart illustrating an example of a data structure of evaluation point data.

FIG. 5B is a chart illustrating an example of a data structure of time-nodal coordinate data.

FIG. 5C is a chart illustrating an example of a data structure of time-evaluation point state data.

DESCRIPTION OF EMBODIMENTS

Hereinafter, modes for carrying out the present invention will be described with reference to the attached drawings.

In this embodiment, a deformation analysis of a material is performed by using FEM (Finite Element Method). Further, fracture determination is performed based on a stress FLD. When a fracture occurs in a certain element (actually, a certain evaluation point that the element has), the element is not eliminated at once but rigidity of the element is gradually decreased, and at a point in time at which the rigidity is decreased to some degree, the element is eliminated. The rigidity decrease of the element is expressed by manipulating a stress applied to the element. Concretely, it is expressed by the following expression based on the concept of continuum damage mechanics.

$$\sigma = (1-D)\sigma' \quad \text{(expression 1)}$$

Here, $\sigma$ is a stress with the rigidity decrease taken into consideration, D is a damage variable (note that $0 \leq D \leq 1$) in the continuum damage mechanics, and $\sigma'$ is a stress with the rigidity decrease not taken into consideration. According to the expression 1, as the damage variable D becomes larger, the stress $\sigma$ with the rigidity decrease taken into consideration becomes smaller.

The continuum damage mechanics is a mechanical theory for analyzing development processes of damage and breakage of materials from a continuum mechanics point of view. In the continuum damage mechanics, a damage state is modeled by using an appropriate macromechanical damage variable, and by using this damage variable, a mechanical behavior and the progress of the damage of the damaged material are described. The progress of the damage is described by the following expression, for instance.

[Mathematical Expression 1]

$$D' = \frac{Y}{S} p' H(p - p_D) \quad \text{(expression 2)}$$

Here, D' is a rate of change of the damage variable D (damage speed), Y is a damage-associated variable, S is a material constant, p is a cumulative plastic strain, p' is a rate of change of the cumulative plastic strain, $p_D$ is a threshold value of the cumulative plastic strain p, and H( ) is a Heaviside function. Then, when the damage variable D increases to reach a critical value $D_c$, that is, when the following expression holds, it is thought that a crack occurs or a breakage occurs.

[Mathematical Expression 2]

$$D = \int_0^t D' dt = D_C \quad \text{(expression 3)}$$

The damage variable D can be interpreted as a rate of decrease of a load-carrying effective area accompanying the progress of micro-distributed voids in a damaging process. The reduction of the load-carrying effective area increases an effect of the stress $\sigma$ caused by an external force. This increased stress (effective stress) $\sigma'$ is described by the following expression.

$$\sigma' = \sigma/(1-D) \quad \text{(expression 4)}$$

The expression 1 is derived from this expression 4.

Figure 1A:
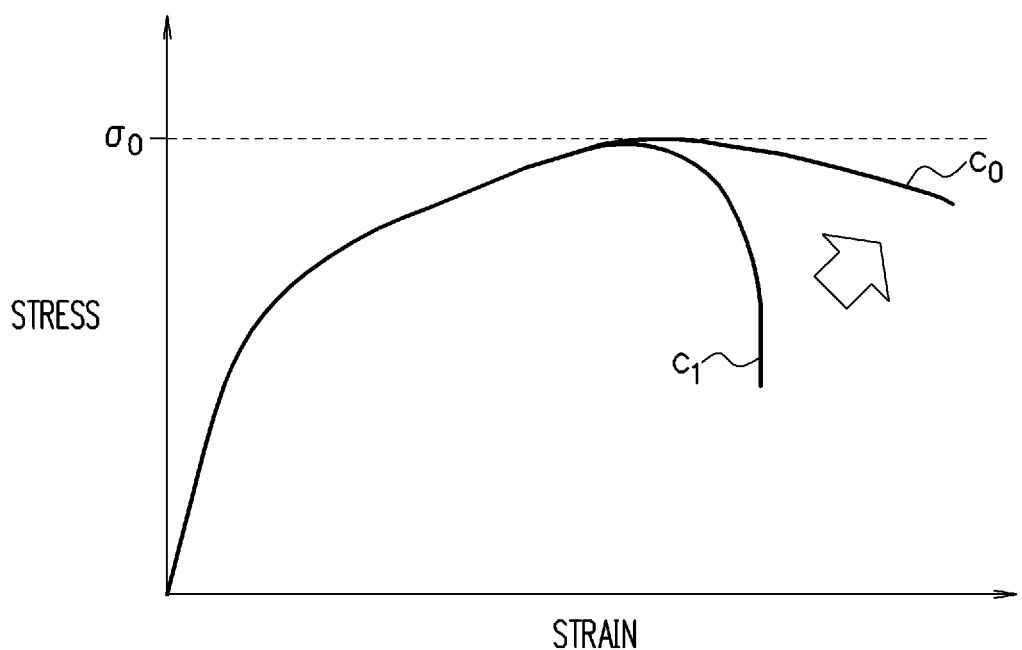
FIG. 1A is a chart illustrating a stress-strain relation $c_0$ obtained by an experiment and a stress-strain relation $c_1$ obtained by a conventional method.
Figure 1B:
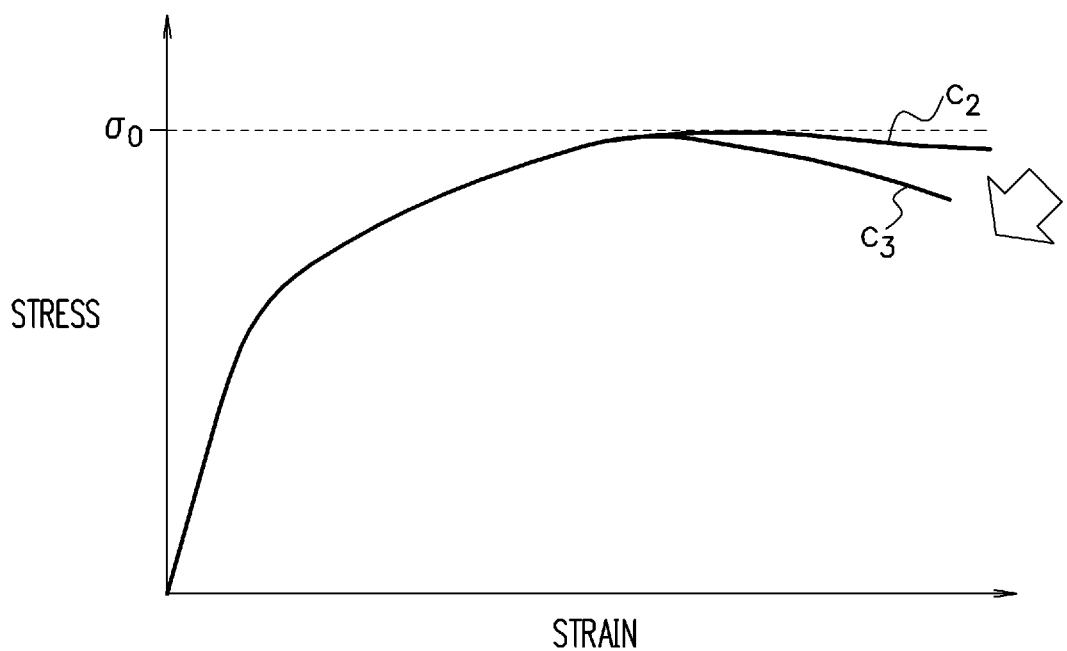
FIG. 1B is a chart illustrating a stress-strain relation $c_2$ with a rigidity decrease not taken into consideration and a stress-strain relation $c_3$ obtained by the present method (with the rigidity decrease taken into consideration).

FIG. 1A and FIG. 1B are charts illustrating the concept of the present invention.

FIG. 1A illustrates a stress-strain relation $c_0$ obtained by an experiment and a stress-strain relation $c_1$ obtained by a conventional method (a method of eliminating an element incurring a fracture). Here, the horizontal axis represents the strain and the vertical axis represents the stress. Further, a stress $\sigma_0$ represents a fracture limit stress. As indicated by the arrow in FIG. 1A, an object of the present invention is to make the curve $c_1$ approximate to the curve $c_0$.

Therefore, when a fracture occurs in a certain element, this element is not eliminated but rigidity of this element is gradually decreased to realize the above. FIG. 1B illustrates a stress-strain relation $c_2$ with a rigidity decrease not taken into consideration and a stress-strain relation $c_3$ obtained by the present method (with the rigidity decrease taken into consideration). Here, the horizontal axis represents the strain and the vertical axis represents the stress. Further, a stress $\sigma_0$ represents a fracture limit stress. As indicated by the arrow in FIG. 1B, by gradually decreasing the rigidity of the fractured element, it is possible to obtain the curve $C_3$.

FIG. 2 is a diagram illustrating an example of a schematic structure of an analysis device 1 which performs such an analysis.

Based on programs stored in a storage unit 12 in advance, the analysis device 1 executes various kinds of processes with reference to data also stored in the storage unit 12 and/or data stored in another not-illustrated device. Further, the analysis device 1 executes the various kinds of processes according to an instruction input by a user via an operation unit 13 and outputs the results to a display unit 14. For this purpose, the analysis device 1 includes a communication unit 11, the storage unit 12, the operation unit 13, the display unit 14, and a processing unit 15.

The communication unit 11 includes a communication interface circuit for connecting the analysis device 1 to a not-illustrated network. Further, the communication unit 11 supplies the processing unit 15 with data received from not-illustrated other devices via the network. Further, the communication unit 11 transmits data supplied from the processing unit 15, to other devices via the network.

The storage unit 12 includes at least one of, for example, a semiconductor memory, a magnetic disk device, and an optical disk device. The storage unit 12 stores an operating system program, driver programs, application programs, data, and so on which are used in the processing in the processing unit 15. For example, the storage unit 12 stores, as the driver programs, an input device driver program which controls the operation unit 13, an output device driver program which controls the display unit 14, and the like. Further, the storage unit 12 stores, as the application programs, an application program which creates analysis data, an application program which performs the deformation analysis of a material, and the like. Further, the storage unit 12 stores, as the data, the analysis data indicating a target, a condition, and so on of the analysis, limit curve data indicating a fracture limit stress curve, end time data indicating an end time of the analysis, and the like. Further, the storage unit 12 stores, as other data, evaluation point data indicating evaluation points of each element, a time counter indicating a current time, nodal coordinate data indicating coordinates of each nodal point at each point in time, evaluation point state data indicating states of the respective evaluation points at each point in time, and the like. Further, the storage unit 12 may temporarily store temporary data involved in a predetermined process.

The analysis data are data indicating the target, the condition, and so on of the analysis, and include, for example, analysis model data indicating a shape of a material, material property data indicating material constants, boundary condition data indicating a boundary condition, analysis control parameters involved in the control of the analysis, and so on. The analysis data may be manually input by a user via the operation unit 13, or may be automatically created by the processing unit 15 based on the application program which creates the analysis data.

The analysis model data are data indicating the shape of the material and include, for example, element structure data (FIG. 3A) indicating the nodal points of each of the elements of the material, nodal coordinate data (FIG. 3B) indicating the coordinates of each of the nodal points, and so on.

FIG. 3A to FIG. 3D are charts illustrating examples of data structures of various kinds of data.

FIG. 3A illustrates an example of the data structure of the element structure data. The element structure data includes, for each of the elements, the element number, the numbers of the nodal points that the relevant element has, and so on.

Further, FIG. 3B illustrates an example of the data structure of the nodal coordinate data. The nodal coordinate data includes, for each of the nodal points, the nodal point number, an X coordinate, a Y coordinate, and a Z coordinate of the relevant nodal point, and so on.

Figure 4:
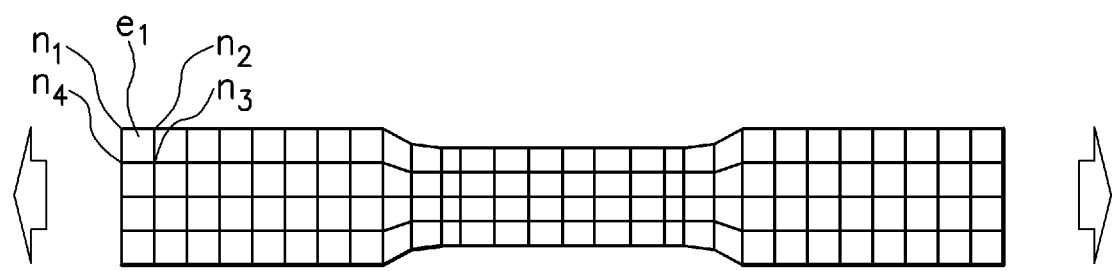
FIG. 4 is a view illustrating an example of a test piece.

FIG. 4 is a view illustrating an example of a test piece displayed based on the analysis model data.

In FIG. 4, a plane view of JIS (Japanese Industrial Standards) No. 5 test piece which is modeled by using a hexahedral element is illustrated.

The material property data is data indicating the material constants and includes, for example, density, a Young's modulus, a Poisson's ratio, and so on.

Further, when the Swift rule of the expression 5 is used as the stress-strain relation, it includes K, $\varepsilon_0$, n, and so on.

[Mathematical Expression 3]

$$\sigma = K(\varepsilon_0 + \varepsilon)^n \quad \text{(expression 5)}$$

Incidentally, the stress-strain relation is not limited to this, and may be others (for example, the Voce rule). Further, it does not need to be a form of a constitutive equation, but the stress-strain relation may be approximated poly-linearly and the resultant value may be directly input.

Further, as damage-related constants, D' (damage speed) in the expression 2, $D_c$ (threshold value of a damage degree based on which the presence of the fracture is determined) in the expression 3, and so on are included.

Incidentally, these material constants are decided so that the analysis result of a test (for example, a uniaxial tensile test) agrees with the experimental result. Concretely, (1) initial values of the material constants are decided, (2) a fracture strain and a stress-strain relation are calculated by analyzing the test, (3) it is determined whether or not the fracture strain and the stress-strain relation agree with those obtained by the experiment, (4) if the fracture strain does not agree or the stress-strain relation does not agree, the values of the material constants are changed, and (5) (2) to (4) are repeated until the fracture strain and the stress-strain relation both agree, whereby the material constants are adjusted.

However, since accuracy of the stress-strain relation decreases especially around the fracture stain, its comparison is performed at a point in time of or before the maximum stress point at which a damage does not occur.

The boundary condition data are data indicating the boundary condition and include, for example, displacement condition data (FIG. 3C) indicating a displacement condition, load condition data (FIG. 3D) indicating a load condition, and so on.

FIG. 3C illustrates an example of the data structure of the displacement condition data. The displacement condition data includes, for each of the nodal points, the nodal point number, X displacement, Y displacement, and Z displacement of the relevant nodal point, and so on.

Further, FIG. 3D illustrates an example of the data structure of the load condition data. The load condition data includes, for each of the nodal points, the nodal point number, an X load, a Y load, and a Z load of the relevant nodal point, and so on.

Returning to FIG. 2, the operation unit 13 may be any device provided that it is capable of operating the analysis device 1, and is, for example, a keyboard, a touch pad, or the like. A user can input characters, numbers, and so on via the operation unit 13. When operated by a user, the operation unit 13 generates a signal corresponding to this operation. Then, the generated signal is supplied to the processing unit 15 as an instruction of the user.

The display unit 14 may be any device provided that it is capable of displaying video pictures, images, characters, and so on, and is, for example, a liquid crystal display, an organic EL (Electro-Luminescence) display, or the like. The display unit 14 displays a video picture, an image, a character, and so on according to video picture data, image data, character data, and so on, respectively, which are supplied from the processing unit 15.

The processing unit 15 is provided with one processor or more and peripheral circuits thereof. The processing unit 15 centrally controls the whole operation of the analysis device 1 and is, for example, a CPU (Central Processing Unit). The processing unit 15 controls the operations of the communication unit 11, the display unit 14, and so on so that various kinds of processes of the analysis device 1 are executed in appropriate procedures according to the programs stored in the storage unit 12, the operation of the operation unit 13, or the like. The processing unit 15 executes the processes based on the programs (the operating system programs, the driver programs, the application programs, and so on) stored in the storage unit 12. Further, the processing unit 15 is capable of executing a plurality of programs (application programs and so on) in parallel.

The processing unit 15 includes a control unit 151, a state variable calculating unit 152, a fracture determining unit 153, and a stress correcting unit 154. These units are functional modules realized by programs executed by the processor included in the processing unit 15. Alternatively, these units may be implemented in the analysis device 1 as firmware.

Hereinafter, processes of the control unit 151 will be described.

When the execution of the application program for the deformation analysis of a material is instructed by a user via the operation unit 13, the analysis device 1 starts the process based on this program.

The control unit 151 realized by this program initializes data. Specifically, the control unit 151 obtains the analysis model data from the storage unit 12, and based on the obtained analysis model data, decides a predetermined number (for example, eight) evaluation points for each element. Then, the control unit 151 creates the evaluation point data (FIG. 5A) indicating the decided evaluation points and stores the evaluation point data in the storage unit 12. Further, the control unit 151 reserves, in the storage unit 12, areas for storing the time counter indicating the current time, time-nodal coordinate data (FIG. 5B) indicating the coordinates of each nodal point at each point in time, and time-evaluation point state data (FIG. 5C) indicating the state of each of the evaluation points at each point in time, and initializes them to "0".

FIG. 5A to FIG. 5C are charts illustrating other examples of the data structures of the various kinds of data.

FIG. 5A illustrates an example of the data structure of the evaluation point data. The evaluation point data includes, for each of the elements, the element number, the numbers of the evaluation points that the relevant element has, and so on.

Further, FIG. 5B illustrates an example of the data structure of the time-nodal coordinate data. The time-nodal coordinate data includes, for each of the nodal points at each point in time, the nodal point number, an X coordinate, a Y coordinate, a Z coordinate of the relevant nodal point, and so on.

Further, FIG. 5C illustrates an example of the data structure of the time-evaluation point state data. The time-evaluation point state data includes, for each of the evaluation points at each point in time, the evaluation point number, a strain and a stress of the relevant evaluation point, a fracture flag indicating whether or not a fracture has already occurred, a damage variable (damage degree), a cumulative damage speed, and so on.

The control unit 151 instructs the state variable calculating unit 152 to execute a process and causes it to calculate the state variables (for example, the strain, the stress, and so on).

The control unit 151 instructs the fracture determining unit 153 to execute a process and causes it to execute the fracture determination based on the stress FLD.

The control unit 151 determines whether or not a fracture has occurred at any of the evaluation points. Specifically, the control unit 151 refers to the time counter stored in the storage unit 12 to obtain the time. Further, the control unit 151 uses the obtained time as a key to refer to the time-evaluation point state data stored in the storage unit 12 and specifies corresponding evaluation points. Then, the control unit 151 determines whether or not the fracture flag of any evaluation point out of the specified evaluation points indicates that the fracture has occurred.

When the fracture has occurred at any of the evaluation points, that is, when the fracture flag of any of the evaluation points indicates that the fracture has occurred, the control unit 151 instructs the stress correcting unit 154 to execute a process and causes it to correct the stress of the evaluation point.

The control unit 151 advances the time by one. Specifically, the control unit 151 refers to the time counter stored in the storage unit 12 to obtain the time. Further, the control unit 151 increments (+1) the obtained time to update the time. Then, the control unit 151 refers to the time counter stored in the storage unit 12 to store the updated time.

The control unit 151 determines whether or not the end time has been reached. Specifically, the control unit 151 refers to the end time data stored in the storage unit 12 to obtain the end time. Then, the control unit 151 determines whether or not the updated time has reached the obtained end time.

When the end time has not been reached, the control unit 151 instructs the state variable calculating unit 152 to calculate the state variables.

On the other hand, when the end time has been reached, the control unit 151 outputs the analysis result. Specifically, the control unit 151 obtains the time-nodal coordinate data and the time-evaluation point state data from the storage unit 12. Then, the control unit 151 outputs the obtained time-nodal coordinate data and time-evaluation point state data to the display unit 14 in a predetermined manner. Then, the control unit 151 ends the process.

Hereinafter, the process of the state variable calculating unit 152 will be described.

The state variable calculating unit 152 obtains the analysis data, the evaluation point data, the time-nodal coordinate data, and the time-evaluation point state data from the storage unit 12 and causes the deformation analysis of the material to progress based on the obtained analysis data, evaluation point data, time-nodal coordinate data, and time-evaluation point state data and calculates the nodal coordinates and the state variables at the current time. Concretely, the state variable calculating unit 152 refers to the time counter stored in the storage unit 12 to obtain the time. Further, the state variable calculating unit 152 uses a time immediately before the obtained time as a key to refer to the time-evaluation point state data stored in the storage unit 12 and obtains the stress of each of the corresponding evaluation points. Further, the state variable calculating unit 152 converts the obtained stresses into loads of the respective nodal points and calculates the displacements (coordinates) of the respective nodal points based on the converted loads. Further, the state variable calculating unit 152 calculates the strains of the respective evaluation points based on the calculated displacements and calculates the stresses of the respective evaluation points based on the calculated strains.

The state variable calculating unit 152 refers to the time-nodal coordinate data stored in the storage unit 12 and stores the calculated coordinates of the respective nodal points in correspondence to the obtained time. Further, the state variable calculating unit 152 refers to the time-evaluation point state data stored in the storage unit 12 and stores the calculated strains and stresses of the respective evaluation points in correspondence to the obtained time. Then, the state variable calculating unit 152 ends the process.

Incidentally, for the deformation analysis, Abaqus (registered trademark) which is a commercial application program is used. However, other application program (for example, OpenFOAM (registered trademark)) can also be used.

With Abaqus (registered trademark), it is possible to find the state variables based on a dynamic explicit method. The dynamic explicit method is a method of solving a dynamic balance equation (equation of motion) with an acceleration term taken into consideration, without iterative calculations. First, by overlapping the equations of motion (expression 6) of the respective elements of the whole material, it is possible to find the equation of motion regarding the whole material.

[Mathematical Expression 4]

$$M \cdot \ddot{u} + P - F = 0 \qquad \text{(expression 6)}$$

Here, M is a mass matrix, u is displacement, P is an equivalent nodal force vector, and F is a nodal external force vector. Next, by solving the found equation of motion, it is possible to find the displacement u. Then, based on the displacement-strain relation and so on, the state variable is found from the found displacement u. Incidentally, to solve the equation of motion, a central difference method which is one of grid point methods is used. However, other solving methods (a forward difference method, a backward difference method, a Lagrange method, a spectral method, and the like) are also usable.

Hereinafter, the process of the fracture determining unit 153 will be described.

Regarding each of the evaluation points where no fracture has occurred, the fracture determining unit 153 calculates the maximum principal stress and the minimum principal stress of the relevant evaluation point based on the stress of the evaluation point calculated by the state variable calculating unit 153. Specifically, the fracture determining unit 153 refers to the time counter stored in the storage unit 12 to obtain the time. Further, the fracture determining unit 153 uses the obtained time as a key to refer to the time-evaluation point state data stored in the storage unit 12 and specifies the corresponding evaluation points. Regarding each of the specified evaluation points, the fracture determining unit 153 refers to the fracture flag of the relevant evaluation point and determines whether or not the fracture flag indicates that the fracture has occurred. Then, when the fracture flag does not indicate that the fracture has occurred, the fracture determining unit 153 extracts the stress of the evaluation point and calculates the maximum principal stress and the minimum principal stress based on the extracted stress.

The fracture determining unit 153 determines whether or not a relation between the maximum principal stress and the minimum principal stress of the evaluation point exceeds the fracture limit stress curve. Specifically, the fracture determining unit 153 obtains the limit curve data from the storage unit 12. Then, the fracture determining unit 153 determines whether or not the relation between the maximum principal stress and the minimum principal stress of the evaluation point exceeds the fracture limit stress curve indicated by the obtained limit curve data.

When the relation between the maximum principal stress and the minimum principal stress of the evaluation point exceeds the fracture limit stress curve, the fracture determining unit 153 determines that the fracture has occurred at the evaluation point and records this. Specifically, when the relation between the maximum principal stress and the minimum principal stress of the evaluation point exceeds the fracture limit stress curve indicated by the obtained limit curve data, the fracture determining unit 153 changes the fracture flag of the evaluation point so that it indicates that the fracture has occurred. Then, the fracture determining unit 153 ends the process.

Hereinafter, the stress correcting unit 154 will be described.

Regarding each of the evaluation points at which the fracture determining unit 153 determines that the fracture has occurred, the stress correcting unit 154 calculates the damage speed of the relevant evaluation point. Specifically, the stress correcting unit 154 refers to the time counter stored in the storage unit 12 to obtain the time. Further, the stress correcting unit 154 uses the obtained time as a key to refer to the time-evaluation point state data stored in the storage unit 12 and specifies the corresponding evaluation points. Regarding each of the specified evaluation points, the stress correcting unit 154 refers to the fracture flag of the evaluation point to determine whether or not the fracture flag indicates that the fracture has occurred. Then, when the fracture flag indicates that the fracture has occurred, the stress correcting unit 154 extracts the number, the strain, and the stress of the evaluation point.

Further, the stress correcting unit 154 uses the time immediately before the obtained time and the extracted evaluation point number as keys to refer to the time-evaluation point state data stored in the storage unit 12 and specifies the corresponding evaluation point. Further, the stress correcting unit 154 extracts the damage degree of the specified evaluation point.

Then, the stress correcting unit 154 calculates the damage speed by using the expression 2 based on the extracted strain, stress, and damage degree.

The stress correcting unit 154 calculates the damage degree of the evaluation point. Specifically, the stress correcting unit 154 extracts the cumulative damage speed of the specified evaluation point. Further, the stress correcting unit 154 adds the calculated damage speed to the extracted cumulative damage speed to update the cumulative damage speed. Then, the stress correcting unit 154 adds the updated cumulative damage speed to the extracted damage degree to update the damage degree. The stress correcting unit 154 stores the updated damage degree and cumulative damage speed as the damage degree and the cumulative damage speed of the evaluation point in the storage unit 12.

The stress correcting unit 154 determines whether or not the damage degree of the evaluation point exceeds the threshold value. Specifically, the stress correcting unit 154 refers to the material property data stored in the storage unit 12 to extract the threshold value of the damage degree. Then, the stress correcting unit 154 determines whether or not the updated damage degree exceeds the extracted threshold value.

When the damage degree of the evaluation point does not exceed the threshold value, the stress correcting unit 154 corrects (decreases) the stress of the evaluation point. Specifically, the stress correcting unit 154 calculates the correction stress by using the expression 1 based on the extracted stress and the updated damage degree. The stress correcting unit 154 stores the calculated correction stress as the stress of the evaluation point in the storage unit 12.

On the other hand, when the damage degree of the evaluation point exceeds the threshold value, the stress correcting unit 154 eliminates the element having the relevant evaluation point. Specifically, the stress correcting unit 154 uses the extracted evaluation point number as a key to refer to the evaluation point data stored in the storage unit 12 and extracts the number of the corresponding element and the numbers of the other evaluation points. Then, the stress correcting unit 154 uses the extracted element number as a key to refer to the element structure data stored in the storage unit 12 and deletes items relating to the corresponding element. Further, the stress correcting unit 154 uses the extracted element number as a key to refer to the evaluation point data stored in the storage unit 12 and deletes items relating to the corresponding element. Further, the stress correcting unit 154 uses the obtained time and the extracted evaluation point numbers as keys to refer to the time-evaluation point state data stored in the storage unit 12 and changes the stresses of the corresponding evaluation points to "0". Then, the stress correcting unit 154 ends the process.

Figure 6A:
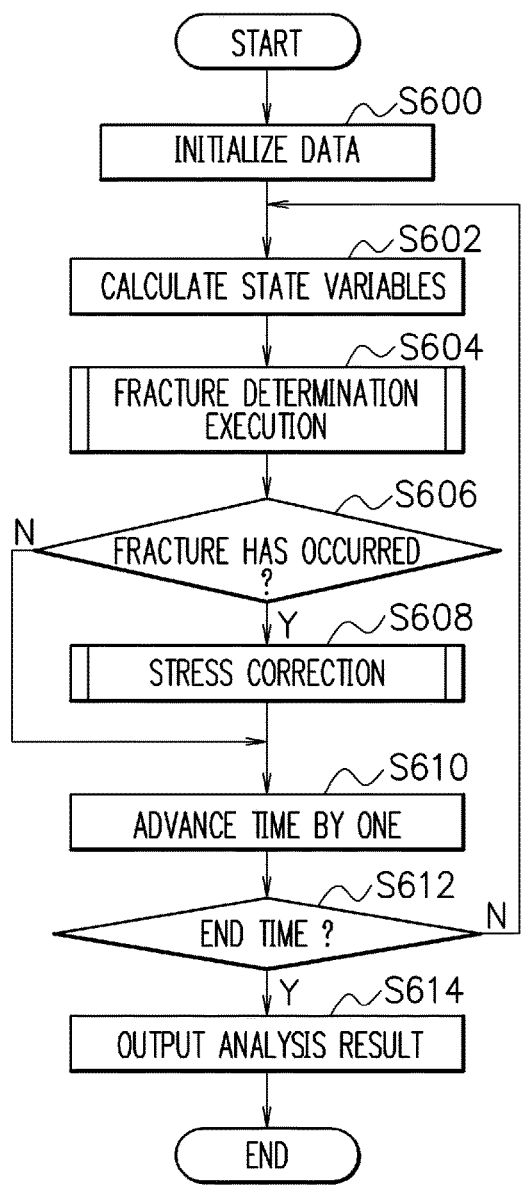
FIG. 6A is a flowchart illustrating an example of an operation flow of the analysis device.
Figure 6B:
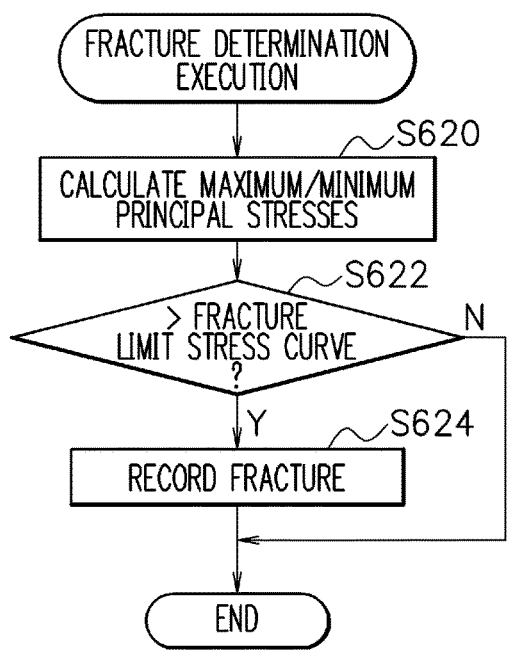
FIG. 6B is a flowchart illustrating an example of a fracture determination execution process.
Figure 6C:
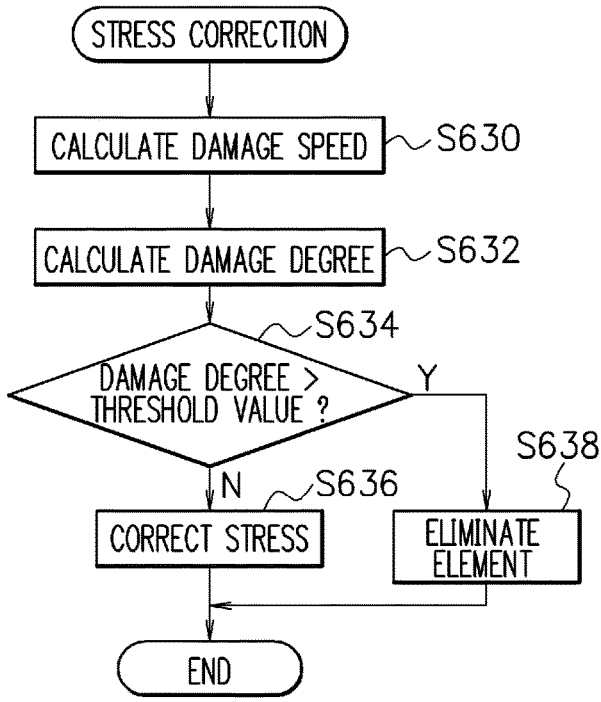
FIG. 6C is a flowchart illustrating an example of a stress correction process.

FIG. 6A to FIG. 6C are charts illustrating examples of operation flows of the analysis device 1. The operation flows described below are executed mainly by the processing unit 15 in cooperation with the elements of the analysis device 1, based on the programs stored in advance in the storage unit 12.

FIG. 6A illustrates an example of the operation flow of the control unit 151.

When the execution of the deformation analysis is instructed by a user via the operation unit 13, the control unit 151 initializes the data (Step S600).

The control unit 151 instructs the state variable calculating unit 152 to execute the process and causes it to calculate the state variables (for example, strain, stress, and so on) (Step S602).

The control unit 151 instructs the fracture determining unit 153 to execute the process and causes it to execute the fracture determination based on the stress FLD (Step S604).

FIG. 6B illustrates an example of the operation flow of the fracture determining unit 153.

Regarding each of the evaluation points at which no fracture has occurred, the fracture determining unit 153 calculates the maximum principal stress and the minimum principal stress of the relevant evaluation point based on the calculated stress of the evaluation point (Step S620).

The fracture determining unit 153 determines whether or not the relation between the maximum principal stress and the minimum principal stress of the evaluation point exceeds the fracture limit stress curve (Step S622).

When the relation between the maximum principal stress and the minimum principal stress of the evaluation point exceeds the fracture limit stress curve (Step S622—Yes), the fracture determining unit 153 records that the fracture has occurred at the evaluation point (Step S624). Then, the fracture determining unit 153 ends the process.

Returning to FIG. 6A, the control unit 151 determines whether or not the fracture has occurred at any of the evaluation points (Step S606).

When the fracture has occurred at any of the evaluation points (Step S606—Yes), the control unit 151 instructs the stress correcting unit 154 to execute the process and causes it to correct the stress of the evaluation point (Step S608).

FIG. 6C illustrates an example of the operation flow of the stress correcting unit 154.

Regarding each of the evaluation points at which the fracture has occurred, the stress correcting unit 154 calculates the damage speed of the relevant evaluation point (Step S630).

The stress correcting unit 154 calculates the damage degree of the evaluation point (Step S632).

The stress correcting unit 154 determines whether or not the damage degree of the evaluation point exceeds the threshold value (Step S634).

When the damage degree of the evaluation point does not exceed the threshold value (Step S634—No), the stress correcting unit 154 corrects the stress of the evaluation point (Step S636).

On the other hand, when the damage degree of the evaluation point exceeds the threshold value (Step S634—Yes), the stress correcting unit 154 eliminates the element including the relevant evaluation point (Step S638). Then, the stress correcting unit 154 ends the process.

Returning to FIG. 6A, the control unit 151 advances the time by one (Step S610).

The control unit 151 determines whether or not the end time has been reached (Step S612).

When the end time has not been reached (Step S612—No), the control unit 151 returns to the calculation instruction of the state variables (Step S602).

On the other hand, when the end time has been reached (Step S612—Yes), the control unit 151 outputs the analysis result (Step S614). Then, the control unit 151 ends the process.

Hereinafter, an example of this embodiment will be described.

In this example, an analysis of a tensile test in which a test piece having the shape illustrated in FIG. 4 (JIS No. 5 test piece) was pulled at a constant speed in the arrow directions was performed. Regarding several patterns of analysis parameters which were different from one another in the presence/absence of the fracture determination based on the stress FLD, the presence/absence of the rigidity decrease of a fractured element, and the magnitude of the damage-related constant, the stress-strain relation was calculated and a degree of the rigidity decrease was confirmed.

Figures 7A, 7B:
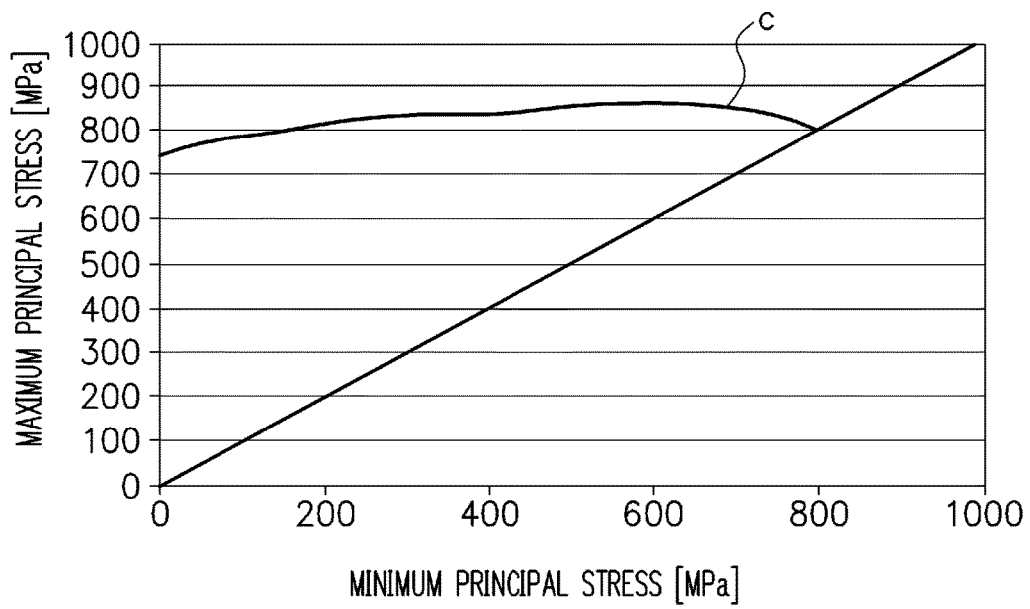
FIG. 7A is a chart illustrating an example of patterns of analysis parameters.
FIG. 7B is a chart illustrating an example of a fracture limit stress curve common to the patterns.

FIG. 7A is a chart illustrating an example of the analysis parameters.

In FIG. 7A, an example of the patterns of the analysis parameters is illustrated. Here, $p_1$ represents a pattern where neither the fracture determination nor the rigidity decrease is performed, $p_2$ represents a pattern where only the fracture determination is performed (conventional method), $p_3$ to $p_5$ represent patterns where both the fracture determination and the rigidity decrease are performed (present method). Further, $p_3$ to $p_5$ represent patterns which are different from one another in the damage-related constant (concretely, the damage speed D'). Note that the other material constants are the same in these patterns.

FIG. 7B illustrates an example of the fracture limit stress curve common to the patterns of the analysis parameters. When the relation between the maximum principal stress and the minimum principal stress exceeds the fracture limit stress curve c, it is determined that the fracture has occurred, and the rigidity decrease is started.

Figure 8:
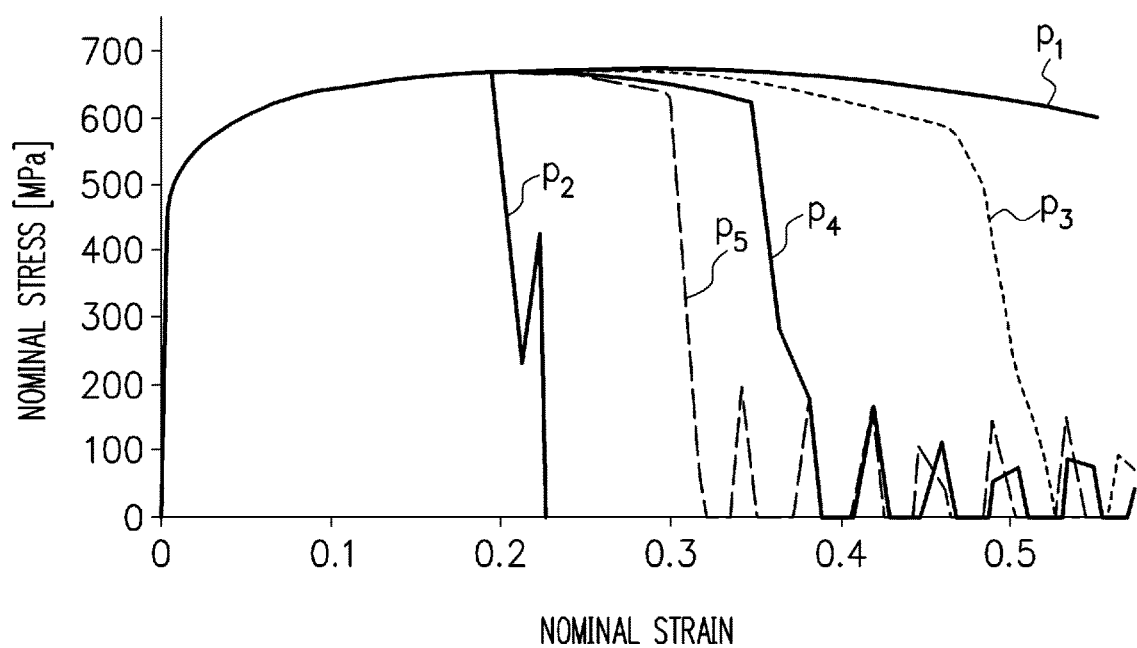
FIG. 8 is a chart illustrating an example of analysis results.

FIG. 8 is a chart illustrating an example of the analysis result.

In FIG. 8, the stress-strain relations calculated for the respective patterns of the analysis parameters are illustrated. Here, the horizontal axis represents a nominal strain and the vertical axis represents a nominal stress. From the stress-strain relations illustrated in FIG. 8, it can be confirmed that, after the fracture occurs, rigidity rapidly decreases in the pattern $p_2$ (conventional method) due to the elimination of the fractured element, while rigidity gradually decreases in the patterns $p_3$ to $p_5$ (present method) due to the reduction of the stress applied to the fractured element. Further, it can be also confirmed that it is possible to adjust the degree of the rigidity decrease depending on the magnitude of the damage-related constant.

As described above, by reducing the stress applied to the element where the fracture has occurred and gradually decreasing the rigidity of the element, it is possible to make a behavior after the fracture occurrence approximate to an actual behavior.

It should be noted that the technical scope of the present invention is not limited to these embodiments and covers the inventions described in the claims and their equivalents.

For example, in this embodiment, the analysis device 1 includes the units illustrated in FIG. 2, but some of them may be included in a not-illustrated server device. For example, the server device may include a storage unit corresponding to the storage unit 12 of the analysis device 1, transmit programs, data, and so on stored in this storage unit to the analysis device 1, and cause the analysis device 1 to execute the processes. Alternatively, the server device may include a storage unit and a processing unit corresponding to the storage unit 12 and the processing unit 15 of the analysis device 1, execute the processes by using programs, data, and so on stored in this storage unit, and provide only the results to the analysis device 1.

Further, a computer program for causing a computer to realize the functions included in the processing unit 15 may be provided in a form of being recorded in a computer-readable recording medium such as a magnetic recording medium or an optical recording medium.

INDUSTRIAL APPLICABILITY

The present invention is applicable to a deformation analysis device, a deformation analysis method, and a program for executing fracture determination based on a stress FLD.

The invention claimed is:

1. A deformation analysis device which calculates a state variable indicating a state occurring in a material according to deformation, the device comprising:
a storage which stores analysis data of the material;
a processing circuitry configured to:
calculate a plurality of state variables of respective elements of the material, and the plurality of state variables includes at least stress, based on the analysis data;
based on the calculated plurality of state variables, determine whether or not a fracture has occurred in each of the elements of the material based on whether or not a relation between a maximum principal stress and a minimum principal stress based on the stress exceeds a fracture limit stress curve which is found in advance for the material;
regarding an element in which it is determined that the fracture has occurred, out of the elements of the material, decrease rigidity of the element in which it was determined that the fracture has occurred, without eliminating the element at once, making the behavior after the occurrence of the fracture approximate to the actual behavior, by calculating a damage variable D in continuum damage mechanics, where D satisfies $0 \leq D \leq 1$, and reducing $\sigma$ by the following expression where $\sigma$ is a stress with a rigidity decrease taken into consideration, and $\sigma'$ is a stress with the rigidity decrease not taken into consideration, $$\sigma = (1-D)\sigma'$$

and correct the stress calculated by the element;
repeatedly perform, by advancing time, calculation of the state variables, determination of an occurrence of the fracture and correction of the stress; and
output the calculated plurality of state variables for a simulation of a press forming or a collision analysis, which are performed in order to search a forming condition in a process of forming a product,
wherein, when the damage variable D exceeds a threshold value, the processing circuitry eliminates the element in which it is determined that the fracture has occurred.

2. A deformation analysis method in which an analysis device including a storage which stores analysis data of a material calculates a state variable indicating a state occurring in the material according to deformation, the method comprising:
calculating a plurality of state variables of respective elements of the material, and the plurality of state variables includes at least stress, based on the analysis data;
based on the calculated plurality of state variables, determining whether or not a fracture has occurred in each of the elements of the material based on whether or not a relation between a maximum principal stress and a minimum principal stress based on the stress exceeds a fracture limit stress curve which is found in advance for the material;
regarding an element in which it is determined that the fracture has occurred, out of the elements of the material, decreasing rigidity of the element in which it was determined that the fracture has occurred, without eliminating the element at once, making the behavior after the occurrence of the fracture approximate to the actual behavior, by calculating a damage variable D in continuum damage mechanics, where D satisfies $0 \leq D \leq 1$, and reducing $\sigma$ by the following expression where $\sigma$ is a stress with a rigidity decrease taken into consideration, and $\sigma'$ is a stress with the rigidity decrease not taken into consideration, $$\sigma = (1-D)\sigma'$$

and correcting the stress calculated by the element;
repeatedly performing, by advancing time, calculation of the state variables, determination of an occurrence of the fracture and correction of the stress; and
outputting the calculated plurality of state variables and, based on the calculated plurality of state variables, searching a forming condition in a process of forming a product or performing a collision analysis,
wherein, when the damage variable D exceeds a threshold value, the element in which it is determined that the fracture has occurred is eliminated.

3. A non-transitory computer readable medium which stores analysis data of a material and a set of instructions, executable by processing circuitry, to execute a method for deformation analysis of calculating a state variable indicating a state occurring in the material according to deformation, the method comprising:
calculating a plurality of state variables of respective elements of the material, and the plurality of state variables includes at least stress, based on the analysis data;
based on the calculated plurality of state variables, determining whether or not a fracture has occurred in each of the elements of the material, based on whether or not a relation between a maximum principal stress and a minimum principal stress based on the stress exceeds a fracture limit stress curve which is found in advance for the material;
regarding an element in which it is determined that the fracture has occurred, out of the elements of the material, decreasing rigidity of the element in which it was determined that the fracture has occurred, without eliminating the element at once, making the behavior after the occurrence of the fracture approximate to the actual behavior, by calculating a damage variable D in continuum damage mechanics, where D satisfies $0 \leq D \leq 1$, reducing $\sigma$ by the following expression where $\sigma$ is a stress with a rigidity decrease taken into consideration, and $\sigma'$ is a stress with the rigidity decrease not taken into consideration, $$\sigma = (1-D)\sigma'$$

and correcting the stress calculated by the element;
repeatedly performing, by advancing time, calculation of the state variables, determination of an occurrence of the fracture and correction of the stress; and
outputting the calculated plurality of state variables for a simulation of a press forming or a collision analysis which are performed in order to search a forming condition in a process of forming a product,
wherein, when the damage variable D exceeds a threshold value, the element in which it is determined that the fracture has occurred is eliminated.

* * * * *